(12) United States Patent
Ross

(10) Patent No.: US 8,512,767 B2
(45) Date of Patent: Aug. 20, 2013

(54) PHARMACEUTICAL COMPOSITIONS

(75) Inventor: Calvin Ross, Cambridgeshire (GB)

(73) Assignee: GW Pharma Limited, Salisbury (GB)

( * ) Notice: Subject to any disclaimer, the term of this patent is extended or adjusted under 35 U.S.C. 154(b) by 0 days.

(21) Appl. No.: 13/606,742

(22) Filed: Sep. 7, 2012

(65) Prior Publication Data
US 2013/0006182 A1   Jan. 3, 2013

Related U.S. Application Data

(60) Continuation of application No. 11/901,593, filed on Sep. 18, 2007, now abandoned, which is a division of application No. 10/221,066, filed as application No. PCT/GB01/01027 on Mar. 9, 2001, now abandoned.

(30) Foreign Application Priority Data

| Mar. 9, 2000 | (GB) | 0005718.2 |
| Jan. 23, 2001 | (GB) | 0101743.3 |
| Jan. 23, 2001 | (GB) | 0101744.1 |

(51) Int. Cl.
*A01N 65/00* (2009.01)

(52) U.S. Cl.
USPC ......................................................... 424/725

(58) Field of Classification Search
None
See application file for complete search history.

(56) References Cited

U.S. PATENT DOCUMENTS

| 3,818,040 A | 6/1974 | Pfister et al. |
| 3,836,541 A | 9/1974 | Johnson et al. |
| 3,836,667 A | 9/1974 | Collier et al. |
| 4,635,651 A | 1/1987 | Jacobs |
| 5,248,493 A | 9/1993 | Brown |
| 5,536,749 A | 7/1996 | Matier et al. |
| 5,976,193 A | 11/1999 | Thomas et al. |
| 6,383,513 B1 | 5/2002 | Watts et al. |
| 6,846,495 B2 | 1/2005 | Dobrozsi et al. |
| 2003/0191180 A1 | 10/2003 | Ross |
| 2008/0071233 A1 | 3/2008 | Ross |
| 2010/0323038 A1 | 12/2010 | Ross |

FOREIGN PATENT DOCUMENTS

| CN | 1116104 A | 2/1996 |
| EP | 000266443 | 5/1988 |
| FR | 2 313 945 A | 1/1977 |
| GB | 2 337 040 A | 11/1999 |
| JP | 75020873 | 7/1975 |
| JP | 403153625 | 7/1991 |
| RU | 2005472 | 1/1994 |
| WO | WO 98/24420 A | 6/1998 |
| WO | WO 00/24362 A | 5/2000 |
| WO | WO 01/03668 A1 | 1/2001 |
| WO | WO 01/13886 A1 | 3/2001 |
| WO | WO 2004/016246 A1 | 2/2004 |

OTHER PUBLICATIONS

Guy et al., A phase one study of sublingual cannabis-based medicine extract. J Pharm Pharmacology. Sep. 2000;52:294.
Marinol capsules web page; printed from http://www.rxlist.com/cgi/generic2/drona.htm, updated Dec. 21, 2004. 2 pages.
Mattes et al., Cannabinoids and appetite stimulation. Pharmacol Biochem Behav. Sep. 1994;49(1):187-95.
Mattes et al., Effects of cannabinoids (marijuana) on taste intensity and hedonic ratings and salivary flow of adults. Chem Senses. Apr. 1994;19(2):125-40.
O'Neil et al., The Merck Index. An Encyclopedia of Chemicals, Drugs, and Biologicals, Thirteenth Edition, Merck Research Labs, Division of Merck & Co., Inc., Whithouse Station NJ. 2001: 292.
Parfitt, Martindale: The Complete Drug Reference. 32nd Edition; Pharmaceutical Press. 1999 Apl;1558:769.
Pearsall, The New Oxford Dictionary of English Oxford University Press. 1998. p. 266.
Tashkin et al., Bronchial effects of aerosolized delta 9-tetrahydrocannabinol in healthy and asthmatic subjects. Am Rev Respir Dis. Jan. 1977;115(I):57-65.
Vachon et al., Airways response to micro-aerosolized delta-9-tetrahydrocannabinol. Chest. 1976;70(3):444.
Williams et al., Bronchodilator effect of delta-tetrahydrocannabinol administered by aerosol of asthmatic patients. Thorax. Dec. 1976;31(6):720-3.

*Primary Examiner* — Michael Meller
(74) *Attorney, Agent, or Firm* — Wolf, Greenfield & Sacks, P.C.

(57) ABSTRACT

The present invention relates to an improved mode of administration for cannabis and its natural and synthetic derivatives. A pharmaceutical composition suitable for sublingual aerosol or spray delivery of cannabis is provided. The formulation may be dispensed using a pump spray or the formulation may include a propellant, such as butane, 1,1,1,2-tetrafluoroethane (HFC-134a) or 1,1,1,2,3,3,3-heptafluoropropane (HFC-227). The term cannabis is used herein to refer to all physiologically active substances derived from the cannabis family of plants and synthetic cannabis analogues and derivatives, precursors, metabolites etc., or related substances having cannabis-like physiological effects.

1 Claim, 4 Drawing Sheets

PHARMACEUTICAL COMPOSITIONS

RELATED APPLICATIONS

This application is a continuation of U.S. patent application Ser. No. 11/901,593, filed Sep. 18, 2007 now abandoned, which application is a division of U.S. patent application Ser. No. 10/221,066, filed May 6, 2003, now abandoned, which is a national stage filing under 35 U.S.C. §371 of international application PCT/GB01/01027, filed Mar. 9, 2001, which was published under PCT Article 21(2) in English, all of which are incorporated herein by reference.

FIELD OF THE INVENTION

The present invention relates to an improved mode of administration for cannabis and its natural and synthetic derivatives. The term cannabis is used herein to refer to all physiologically active substances derived from the cannabis family of plants and synthetic cannabis analogues and derivatives, precursors, metabolites etc., or related substances having cannabis-like physiological effects.

BACKGROUND OF THE INVENTION

The medicinal and psychoactive properties of the cannabis plant have been known for centuries. At present, cannabis is not legally available. However, there is growing pressure on politicians to legalise its use, especially for medicinal purposes.

Evidence suggests that cannabis is a safe, versatile and potentially inexpensive drug. It has been reported as being beneficial to patients suffering from a wide range of symptoms experienced in connection with various, often very serious, medical conditions. For example, cannabis has been used to alleviate symptoms associated with cancer, anorexia, AIDS, chronic pain, spacicity, glaucoma, arthritis, migraine and many other illnesses.

Cannabis is recognised as having anti-emetic properties and has been successfully used to treat nausea and vomiting in cancer patients undergoing chemotherapy.

Studies also report use of cannabis in treating the weight loss syndrome of AIDS and in reducing intraocular pressure for the treatment of glaucoma. Cannabis is also reported to have muscle relaxing effects and anti-convulsant effects.

However, it is also well documented that these medicinal effects of cannabis come at the cost of less desirable effects. It is alleged that the administration of cannabis causes changes in mood, perception and motivation. The common euphoric effects have led to the use of cannabis as a recreational, "soft" drug and its criminalisation. The psychoactive effects are said to vary with dose, with the typical cannabis smoker experiencing a "high" which lasts about 2 hours, during which there is impairment of cognitive functions, perception, reaction time, learning and memory. These side effects clearly have implications, such as for the operation of machinery, and in particular for driving. These effects also make cannabis less attractive for widespread, mainstream use, as it can reduce a patient's ability to perform relatively simple tasks during treatment.

The euphoric effects of cannabis may also constitute an undesirable side effect for patients using the drug for medicinal purposes, especially for "naive" cannabis users. Furthermore, here have been reports of unpleasant reactions to cannabis, such as anxiety, panic or hallucinations. It is believed that these undesirable effects are most commonly associated with higher doses of cannabis.

Despite these effects, years of research have failed to show that cannabis is dangerous. In fact, the results appear to have proved the opposite. Cannabis has been shown to be safer, with fewer serious side effects than most prescription drugs currently used as anti-emetics, muscle relaxants, hypnotics and analgesics, etc.

The physiological and pharmacological effects of cannabis depend upon a number of factors, including the dosage level and the route of administration.

There are currently two main methods of cannabis delivery. Lung delivery is most commonly achieved by smoking cannabis. Unfortunately, there are concerns about the effect of this mode of administration on the lungs. Cannabis smoke carries even more tars and other particulate matter than tobacco, and so may be a cause of lung cancer. Furthermore, many patients find the act of smoking unappealing, as well as generally unhealthy. It is known that some of the chemicals produced by smoking cannabis are aggressive and smoking has been shown to cause the gradual dissolving of teeth. For these reasons, smoking is not an approved medical means of administration for any drug.

Attempts have been made to overcome some of the problems associated with smoking both cannabis and tobacco by providing various smokeless inhalable aerosol formulations for lung delivery. A self-propelled inhalable aerosol of delta-9-tetrahydrocannabinol was developed as long ago as 1975 as a bronchodilator. Inhalable aerosol formulations were made comprising either only liquid components and or including a solid particulate component carrying the active agent, such as the cannabis. The various formulations were found to be of varying effectiveness in delivering the active agent to the alveoli of the lungs in the same manner as smoke.

However, both methods of lung delivery discussed above have been found to cause a pronounced and involuntary cough, possibly from irritation of the trachea and lungs. This unpleasant side effect is not overcome by the smoke-free method of lung delivery.

An oral dosage form of cannabis is available in the United States as a Schedule II drug. The capsules contain a synthetic version of delta-9-tetrahydrocannabinol (delta-9-THC), the main active substance in cannabis, and they have had limited success for a number of reasons. Firstly, in light of its anti-emetic properties, the capsules are commonly used to treat nausea and vomiting. Clearly, an oral administration is not ideal as the patient may well have difficulty keeping the capsule down long enough for it to take effect. It has also been found that orally administered THC is erratically and slowly absorbed into the bloodstream, making the dose and duration of action difficult to control. Furthermore, the oral dose is less effective than smoked cannabis and therefore larger doses are required in order to achieve a desired therapeutic effect.

SUMMARY OF THE INVENTION

The applicants have discovered that an alternative mode of administration allows the clinical or medicinal effects of cannabis to be maximised, whilst reducing the above discussed unpleasant and negative side effects. According to the present invention, the cannabis is formulated for sublingual delivery in aerosol or spray form, which offers unexpected advantages over known modes of cannabis delivery. The invention also relates to a device for delivering such a composition as an aerosol or spray.

Formulations according to the invention may include a propellant or may be dispensed using a pump spray device. The spray or aerosol devices may have upright or inverted valves. Furthermore, the aerosol or spray device may be adapted specifically for sublingual delivery. For example, the mouthpiece of the device may be adapted to direct the sprayed dose towards the sublingual mucosa. The device may also be adapted to dispense particles of a particular size, thereby optimising the sublingual uptake.

It is known that sublingual delivery of a pharmaceutically active agent results in fast uptake. The active agent is administered to the sublingual mucosa, from which it is rapidly absorbed into the bloodstream. Sublingual delivery also avoids first-pass metabolism of the active agent.

Aerosol or spray delivery of a composition to the sublingual area is particularly convenient and effective, and promotes fast-uptake. The sprayed composition will be thinly spread over the sublingual area, so that more of the dispensed composition will be absorbed and will be absorbed more quickly than where sublingual delivery is by some other mode, such as, for example, allowing a tablet to dissolve under the tongue.

The fast onset of the therapeutic effects of sublingually administered cannabis has the advantage of providing fast relief from the symptoms to be treated. It also has the advantage of reducing the risk of excessive doses being administered in an attempt to get immediate relief from symptoms, which is often observed in connection with slow-acting active agents and means of administration and which is potentially dangerous.

Sublingual delivery is clearly more attractive than injection, as alternative method of delivery offering fast uptake. Injection is painful, especially when regular administration is required. It can also be difficult for a patient to inject themselves, especially if weak or lacking co-ordination, often making it necessary for someone other than the patient to perform the administration.

Sublingual delivery also has advantages over oral delivery. It is well suited for administration of anti-emetics, it having rapid onset and delivery is not affected by nausea and vomiting. A sublingual dose is also absorbed at a predictable rate and so its administration can be accurately controlled. Devices with metered valves may be used to dispense the active agents sublingually, allowing accurate volumes, and therefore accurate doses, to be dispensed.

Sublingual delivery also avoids the negative effects associated with smoking. The risk of lung cancer due to the tar and impurities drawn into the lung by smoking will be avoided. Furthermore, the pronounced and involuntary cough associated with lung delivery of cannabis is not experienced with sublingual delivery.

A further and unexpected advantage associated with sublingual delivery of cannabis is that it is significantly more effective than smoking (which in turn is known to be significantly more effective than oral delivery). This is surprising in light of the huge surface area of the lungs which would be expected to allow much greater uptake of the cannabis than sublingual delivery which exposes a much smaller surface area to the active agent.

This effectiveness allows some of the undesirable effects of cannabis administration to be avoided, these effects being mainly associated with larger doses. Indeed, the applicants have discovered that the sublingual delivery of cannabis allows the beneficial medicinal effects of cannabis to be enjoyed whilst minimising the negative effects, such as the euphoria and impairment of faculties. That said, the sublingual administration of doses of cannabis large enough to produce said euphoric effect is still possible, if desired.

In one of the preferred embodiments of the present invention, a pharmaceutical composition suitable for sublingual delivery is provided comprising a pharmaceutically active agent which is cannabis and a propellant. The propellant may be, for example, 1,1,1,2-tetrafluoroethane (HFC-134a), 1,1,1,2,3,3,3-heptafluoropropane (HFC-227) or butane. Most preferably, the propellant included in the composition is HFC-134a or HFC-227.

In the past, aerosol or spray formulations frequently included one or more chlorofluorocarbon as a propellant, dichloro-difluoromethane being commonly used. It is well documented that chlorofluorocarbons are implicated in the depletion of the ozone layer and their production, therefore, is being phased out. 1,1,1,2-tetrafluoroethane (HFC-134a) and 1,1,1,2,3,3,3-heptafluoropropane (HFC227) are significantly less harmful to the ozone layer and they are of low toxicity and of suitable vapour pressure for use as aerosol propellants, making then suitable for use in pharmaceutical aerosols. An additional benefit is that HFC-134a and HFC227 can be used in combination with many pharmaceutically active agents, without causing any degradation to them or reducing their physiological activity. They are also not flammable.

Preferably, the composition of the present invention includes a carrier. In a preferred embodiment of the invention, the carrier is a lower alkyl ($C_1$-$C_4$) alcohol, a polyol, or a (poly) alkoxy derivative. In embodiments, the carrier is a $C_1$-$C_4$ alkyl alcohol or a lanolin alcohol and, preferably, is ethanol or isopropyl alcohol. The most preferred alcohol is ethanol.

The preferred polyols include propylene glycol and glycerol and the preferred (poly) alkoxy derivatives include polyalkoxy alcohols, in particular 2-(2-ethoxyethoxy) ethanol (available under the Trademark Transcutol®).

Further preferred (poly)alkoxy derivatives include polyoxyalkyl ethers and esters, such as polyoxyethylene ethers or esters. The preferred polyoxyethylene ethers and esters are polyoxyethylene alkyl ethers, polyoxyethylene castor oil derivatives, polyoxyethylene sorbitan fatty acid esters and polyoxyethylene stearates.

The preferred fatty acid alkyl esters are ethyl oleate, isopropyl myristate and isopropyl palmitate. The preferred polyalkylene glycol is polyethylene glycol.

In preferred embodiments, the inventive composition can comprise up to 50% or, preferably, 25% w/w carrier. More preferred embodiments include between 3% and 15% w/w, or between 4 and 10% w/w carrier. The pharmaceutical compositions can comprise between 50% and 99% w/w, preferably between 75% and 99% w/w, and, more preferably, between 88% and 95% w/w HFC-134a or HFC-227.

In further embodiments, compositions used in the present invention can comprise a plurality of different carriers.

Further excipients can be included in the formulations employed in the present invention. For example, neutral oils as well as surfactants (the latter for aiding the smooth operation of the valve), as are well known to those skilled in the art, may be included.

Thus, in further preferred embodiments, compositions employed in the invention can comprise an organic surfactant. The preferred organic surfactant is oleyl alcohol, although others can be employed, including sorbitan trioleate, sorbitan mono-oleate, sorbitan monolaurate, polyoxyethylene (20) sorbitan monolaurate, polyoxyethylene (20) sorbitan mono-oleate, natural lecithin, oleyl polyoxytheylene (2) ether, stearyl polyoxyethylene (2) ether, lauryl polyoxyethylene (4) ether, block copolymers of oxyethylene and oxypropylene, oleic acid, synthetic lecithin, diethylene glycol dioleate, tetrahydrofurfuryl oleate, ethyl oleate, isopropyl myristate, glyceryl mono-oleate, glyceryl monostearate, glyceryl monoricinoleate, cetyl alcohol, stearyl alcohol, cetyl pyridinium chloride, olive oil, glyceryl monolaurate, corn oil, cotton seed oil or sunflower seed oil.

It is preferable to include a flavouring oil in a formulation to be delivered sublingually. The preferred flavouring oil is peppermint oil, although it is clear that other flavour oils may be used, according to preference.

Some of the preferred compositions for the sublingual delivery according to the present invention contain tetrahydrocannabinols (THCs), such as delta-9tetrahydrocannabinol, the major active constituent of cannabis.

Many of the readily available substances derived from the cannabis plant are extracted in liquid form which may itself be directly sprayed using a pump spray or which may be soluble directly in the propellant, whilst other cannabis forms need to be solubilised in a co-solvent, such as ethanol, thus causing or allowing all or a proportion of the active agent present in the composition to dissolve and/or remain in solution, even after it has been dispensed.

The pharmaceutical compositions can be partial solutions in which only a proportion of the pharmaceutically active agent present therein is dissolved in the propellant and co-solvent, with the remainder being in suspension or suspendible. The exact proportions of dissolved and suspended active agent will depend upon the active agent concerned, its concentration and the identity and quantity of the co-solvent (s) used. In preferred embodiments the compositions are in the form of liquid solutions when maintained under pressure in devices in accordance with the invention.

In a particularly preferred embodiment of the invention the composition comprises a solution of delta-9-tetrahydrocannabinol in ethanol as a co-solvent and HFC-134a as a propellant.

The compositions of the present invention may also comprise cannabis in combination with other pharmaceutically active agents. For example, a formulation particularly suitable for providing improved anti-emetic effect comprises cannabis as the primary agent, with corticosteroid as a supplemental agent. In order to decrease toxicity of the primary agent, cannabis may be formulated together with the supplemental agent phenothiazine. Concurrent use of cannabis with prochlorperazine in low doses can reduce incidence of dysphoria which can accompany the administration of cannabis.

According to a further aspect of the invention, devices for delivering the cannabis compositions of the first aspect of the invention are provided.

Devices for administering metered aerosol doses of pharmaceutical preparations are well known in the art. Such devices include those disclosed in WO 92/11190, U.S. Pat. No. 4,819,834 and U.S. Pat. No. 4,407,481. Many of these devices include metering valves having components formed from plastic materials, such as the valves available from Bespak PLC of Bergen Way, Kings Lynn, Norfolk PE30 2JJ, United Kingdom, in which the valve core, metering chamber and some other structural components are formed from plastic materials. The plastic materials currently used for forming these structural parts in valves employed with many chlorofluorocarbon containing formulations include certain acetal co-polymers.

Although the plastics employed to manufacture metering valves, including the aforementioned acetal co-polymers, have also been found to be stable in the presence of HFC-134a alone, the applicants, to their surprise, have determined that many of these plastics materials can be caused to swell in the presence of formulations which include certain carriers or active agent solubilising co-solvents with HFC-134a. When such swelling takes place in a valve, the fit of mutually slidable components, such as metering chambers and valve cores, is adversely effected and they can bind together or become loose, causing the valve to leak or cease functioning altogether.

This problem has now been solved by using a device for providing pharmaceutical doses comprising a container, filled with a pharmaceutical composition including a pharmaceutically active agent in a solution of liquefied HFC-134a, or HFC-227, and a carrier selected from pharmaceutically acceptable alcohols, polyols, (poly)alkoxy derivatives, fatty acid alkyl esters, polyalkylene glycols, and dimethylsulphoxide, and valve means arranged for delivering aerosol doses of said pharmaceutical composition to the exterior of the container, wherein at least a portion of the device is formed from a polyester. Preferably, the valve means includes at least one component formed from a polyester, which component, more preferably, is a metering chamber and/or a valve core.

In further embodiments, the container comprises a polyester and, preferably, consists of metal lined with a polyester. The canister cap can also be so formed.

Apart from allowing the aforementioned swelling problem to be solved, an advantage of this aspect of the present invention is that use of expensive metal valve components can be avoided.

The preferred polyesters are polyalkylene benzene dicarboxylates, more preferably polyalkylene terephthalates and, most preferably, a polybutylene terephthalate.

Such materials, preferably, have a density of about 1.3 g/cm$^3$ and a water absorption of about 0.6% (23° C. saturation). The polyesters, also, are preferably partially crystalline in nature and have a crystalline melting range of 220-225° C.

Examples of suitable polybutylene terephthalates include those available under the Trademark Celanex® from Hoechst UK Limited, Walton Manner, Milton Keynes, Bucks MK7 7AJ, United Kingdom. Particularly preferred are Celanex® 2500 and Celanex® 500/2.

A variety of types of conventional spray devices exist are able to dispense very accurate volumes. However, this alone cannot ensure administration of a specific dose.

When pharmaceutical compositions are administered sublingually, it is particularly important that they are accurately delivered to the sublingual area. The sublingual area is relatively small and can be hard to reach because of the position under the tongue. If the composition does not come into contact with the sublingual mucosa, it will not be quickly absorbed and, indeed, may not be directly absorbed at all. This will clearly lead to an inaccurate dose being administered and the patient not receiving the desired amount of pharmaceutically active agent.

Therefore, a problem associated with sublingual administration of pharmaceutical compositions is the difficulty ensuring that a predictable dose is brought in contact with the sublingual mucosa. This can be particularly problematic where the composition is delivered by spray delivery. There are various factors which particularly influence the ability to ensure that a dispensed composition contacts the relatively small area of the sublingual mucosa.

Firstly, the direction and spread of the sprayed composition are clearly relevant. If the sprayed composition spreads or disperses upon leaving the aerosol or spray device, it is likely to contact a large area of the oral cavity other than the sublingual mucosa. This will make it unlikely that all of the composition will be absorbed and some of the active agent will not have an effect, thereby effectively reducing the dose administered.

Secondly, the velocity at which the composition is dispensed will also play a role, as the sublingual mucosa will be relatively close to the dispensing device when in use. If the composition is travelling at high velocity when it enters the oral cavity, it is more likely to spread around the cavity, rather than coming into contact almost exclusively with the sublingual mucosa, as desired.

At present there are no bespoke spray devices for sublingual administration. Rather, conventional spray devices of various types are generally used, and the user must attempt to direct the spray to the sublingual area.

The majority of known, conventional spray devices basically comprise a container in which the composition is stored, the composition being dispensed from an orifice or outlet, wherefrom it is allowed to generally disperse, often creating a cloud of droplets of dispensed composition. When using such devices for sublingual delivery, the user can, at best, attempt to control the general direction in which the composition is dispensed by pointing the device as a whole in a certain direction. However, it will be difficult, if not impossible, to target a small area like the sublingual mucosa, especially as it is positioned under the tongue.

Many conventional spray devices use a propellant, wherein the composition is dispensed through a single orifice. This generally results in the composition being dispensed at high velocity which, as discussed above, is undesirable in sublingual spray delivery.

An example of a conventional spray device generally capable of dispensing accurate doses is device is a so-called metered dose inhaler, or MDI device, frequently used to dispense pharmaceuticals for the treatment of asthma or angina and which has an inverted valve. A conventional MDI device comprises a pressurised aerosol container, carrying the composition to be administered for inhalation therapy. The container is encased in a housing which includes a mouthpiece and a passage leading from the orifice or outlet of the container to the mouthpiece. The mouthpiece is shaped to be comfortably held between the lips when the pharmaceutical composition is dispensed.

The MDI devices currently available are specifically intended for lung delivery. The dispensed composition is directed to the back of the throat, and inhalation by the patient results in the composition being drawn into the lungs from the oral cavity. Whilst MDI devices can dispense accurate and reproducible doses, such devices are not well suited to sublingual delivery for two reasons. Firstly, the devices are shaped to direct the dispensed substance to the back of the throat and not under the tongue. Secondly, because the substance is inhaled, it is dispensed at high velocity.

Thus, in a preferred embodiment of the present application, a spray or aerosol device has a bespoke mouthpiece, the mouthpiece being adapted to channel and direct the dispensed composition according to the present invention from an orifice of the device, towards the sublingual area of the user. Such a mouthpiece could be used in conjunction with a conventional spray device, such as one of the types discussed above.

Preferably, the mouthpiece of the dispensing device is angled in relation to the main body of the device, so that the mouthpiece directs the dispensed composition to the sublingual mucosa when the device is activated whilst held in the normal position for use.

Such a mouthpiece could be used in conjunction with devices having either an upright or an inverted valve. In a preferred embodiment, the device has an inverted valve, such devices generally being capable of dispensing accurate volumes of composition.

According to a further preferred embodiment, the mouthpiece for directing the dispensed composition to the sublingual area is part of a housing in which the main body, including the container, of the spray device is held. The mouthpiece could be rigidly fixed with respect to the housing, or the connection between the housing and the mouthpiece could be flexible, allowing the angle of the mouthpiece relative to the main body of the device to be adjusted.

In a further embodiment, the mouthpiece is shaped in such a way that it assists directional dispensing of the composition to the sublingual area of the mouth.

Preferably, the mouthpiece is long enough to allow the opening of the mouthpiece to sit under the tongue when the composition is dispensed. This will reduce the amount of composition being dispensed to parts of the oral cavity other than the sublingual area. Even more preferably, for greater comfort and greater ease of use, the mouthpiece is also a slim shape, fitting comfortably under the tongue or being comfortably held to direct the spray towards the sublingual area.

Additionally, the mouthpiece may also be shaped in such a way that it discourages the spread of the dispensed composition after it leaves the mouthpiece. As discussed above, when a composition is dispensed by a conventional spray device it will generally spread, forming a cloud. This is undesirable where a small area of the oral cavity is to be targeted. In a preferred embodiment, the mouthpiece opening is no larger than the average size of the sublingual area. This means that, despite some degree of spreading of the dispensed composition after it has left the mouthpiece, the spread will be limited to ensure that the area of the oral cavity contacted by the dispensed composition will correspond generally to the sublingual area, provided the composition is dispensed in the correct direction.

It is also advantageous for the dispensing device to be adapted to reduce or control the velocity at which the dispensed composition leaves the device. This will help to ensure that the composition comes into contact with the sublingual mucosa and stays in contact for long enough for the pharmaceutically active agent to be absorbed. Such control may be provided, to an extent, by the shape of the mouthpiece of the dispensing device.

Thus, in accordance with a further preferred embodiment of the present invention, the mouthpiece of the spray device has a cross-sectional area which first gradually increases, and then decreases. The resultant "duckbill" shape will both control the velocity of the dispensed composition and limit its spread. It is clear that a variety of mouthpiece shapes may be used to reduce the velocity of the dispensed composition.

In another preferred embodiment, the velocity with which the composition is dispensed is also reduced by providing the device with a plurality of orifices through which the composition is released. The provision of more than one orifice will reduce the force with which the dispensed composition is released from the main body of the device, thereby reducing its exit velocity. The more orifices through which the composition is dispensed, the slower the velocity of the substance dispensed.

In a yet more preferred embodiment, in a device having a plurality of orifices these orifices may be shaped and positioned to be directional, preferably serving to direct the individual jets of dispensed composition toward on another, to avoid unnecessary and undesirable spreading of the composition around the oral cavity.

Most preferably, the orifices are directed so that jets of dispensed composition converge at a point which is approximately the same distance from the nozzle of the device as the sublingual area will be from the nozzle when the device is used. Thus, the composition should contact a relatively small area, avoiding wastage caused by the composition being dispensed to areas other than the sublingual mucosa.

In a preferred embodiment of the invention, the orifices of the device are further adapted to dispense particles of a particular size, thereby optimising absorption across the sublingual mucosa.

A problem sometimes encountered with conventional spray and aerosol devices is that there is some degree of interaction between the container and the composition stored therein. This interaction can be in the form of corrosion of the container by the composition, or leaching of materials from the container into the composition, both of which are clearly undesirable. Such interaction between the container and its contents can significantly curtail the shelf life of the container. Furthermore, resultant contamination of the composition can be dangerous. Even seemingly inert compositions may eventually interact with their container when stored for prolonged periods.

Such interaction between the container and the contents thereof is a particular problem with the compositions of the present invention because cannabis and its analogues and derivatives are highly corrosive. Thus, these compositions cannot be stored in convention metal containers for any significant length of time.

It has been found that glass containers are considerably more resistant to interaction with compositions than the conventionally used metal and plastic containers. Therefore, in a further preferred embodiment of the present invention, the devices for spray dispensing the compositions of the invention include glass containers within which the composition is stored.

Preferably, in order to provide additional protection against interaction, the internal surface of the glass container may be coated. The coated containers will have surface properties like quartz, being highly inert. In a particularly preferred embodiment, the surface of the glass container is coated with a chemically bonded, ultra thin layer of pure silicone oxide. The thickness of such a layer would preferably be between 0.1 and 0.2 microns. Such a layer may be applied by a process whereby the inner surface of the container is first activated using pure oxygen. Next, silicone oxide coating gas is introduced into the container. Then, a plasma reaction is initiated by microwave energy, leading to the formation of a silicon oxide layer on the inner surface of the glass container.

Clearly, other inert coatings applied to the glass container surface may also protect the glass from interaction with the composition to be stored therein. The effect of such coatings is particularly apparent over time, the coating providing an inert barrier between the glass container and the composition stored therein.

A further advantage of glass containers is that it is much harder to tamper with them than with conventional containers. The provision of a tamper-proof container for pharmaceutical compositions as it will make it very difficult to gain access to the composition. It is particularly desirable to prevent extraction of the composition from the container where the pharmaceutical composition is one which is open to abuse, like the compositions of the present invention.

Containers made from conventional materials such as metals, such as aluminium, or plastics, are vulnerable to tampering. These materials may be punctured, for example with a syringe, and the pharmaceutical composition within the container can be extracted or material can be added to the contents of the container. In some circumstances, such tampering may even go unnoticed.

In contrast, glass cannot be punctured in this manner. Indeed, due to its tendency to break or shatter, it will be very difficult, if not impossible to tamper with a glass container, without destroying the container. A pressurised glass container in an aerosol or spray device will be particularly difficult to tamper with. Such containers will be pressurised, for example to a pressure of 6-8 bar and are prone to actually explode if tampered with, as the glass having a tendency to crack or shatter, as discussed above. This will make it virtually impossible for the contents of the container to be collected.

In order to reduce the risk of accidentally breaking of the relatively fragile glass container during normal use, it is preferably encased in a protective housing. Such a housing will reduce the risk of the container breaking by accident, for example when dropped.

One further advantage obviously afforded by using a container made from glass is the fact that it is transparent. Thus, the contents of the container are potentially visible. When the container is encased in a housing, the housing could be provided with a window, or could be transparent itself, in order to allow the container contents to be viewed.

Being able to see the amount of the composition left in the container can be very useful, especially where the composition is one which the user relies upon heavily, so that it would be highly undesirable for the composition to unexpectedly run out. For example, where the container contains a strong painkiller, it would be highly undesirable for the patient to only realise that the composition has run out when they require a further dose which is not available. Where the patient can see the composition inside the container, it will be easier to ascertain when the supply of composition is about to run out and when it will be necessary to obtain more.

According to a preferred embodiment of the present invention, to further assist monitoring of the amount of composition left in a container, the container is provided with markings to show how many doses are left inside the container. Thus for example, a warning line is provided, indicating that it is time to obtain more composition when the level inside the container reaches that line. Alternatively, where the container is encased in a housing, the markings are on the housing, preferably adjacent to the container.

Some examples of devices for sublingual delivery of cannabis will now be described, by way of example only, and with reference to the following drawings.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION OF THE INVENTION

Figure 1:
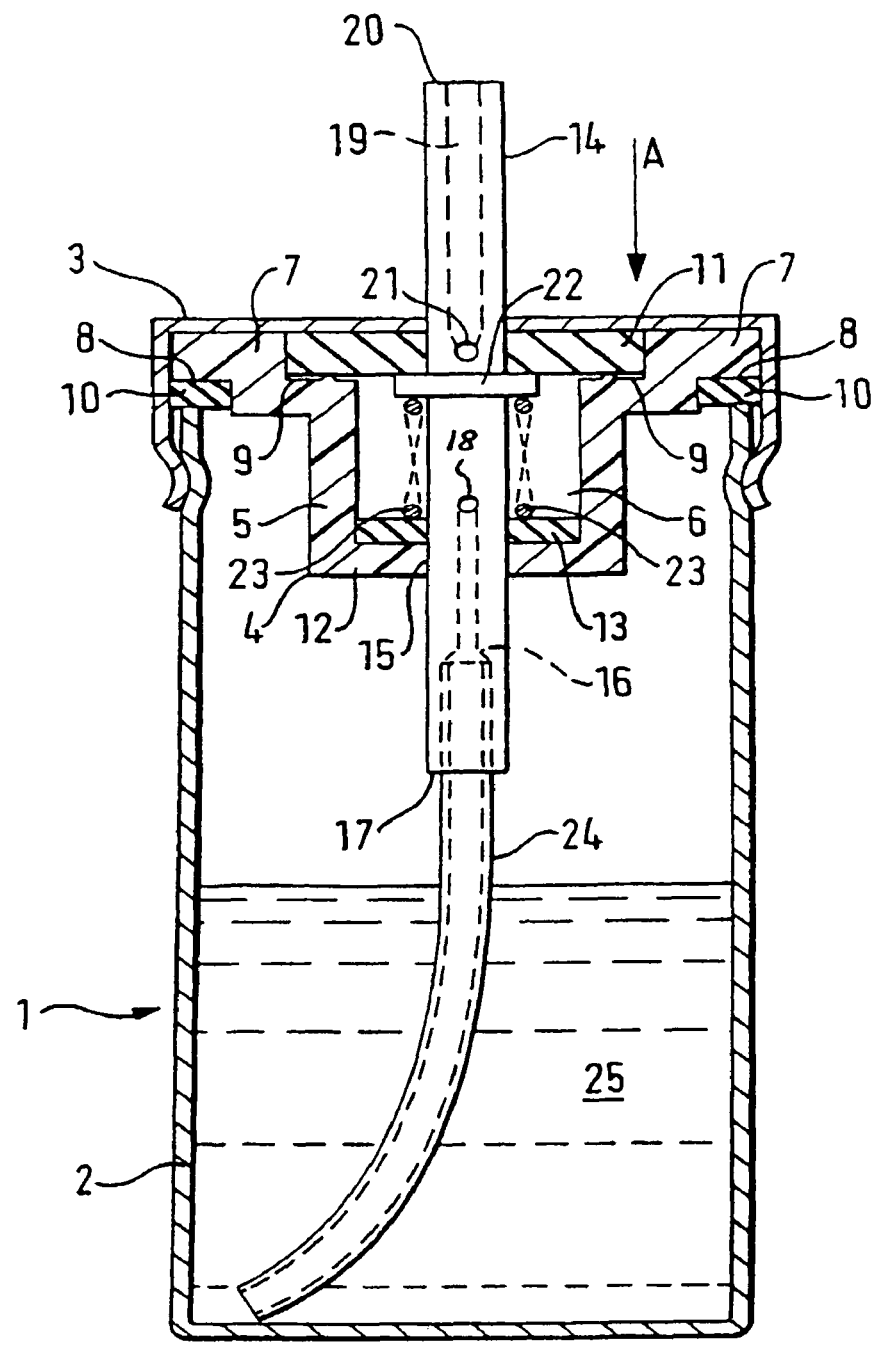
FIG. 1 is a cross sectional view of an embodiment of a device in accordance with the invention, the device having an upright valve.
Figure 2:
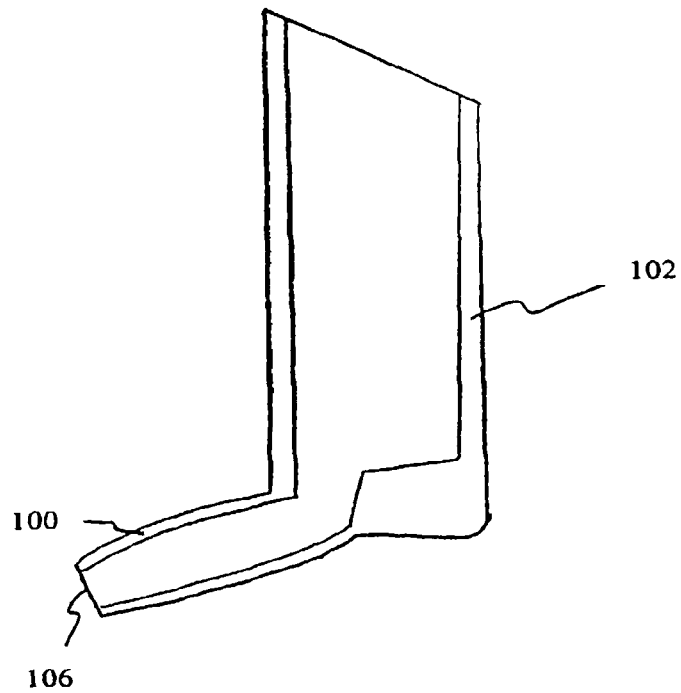
FIG. 2 is a cross sectional view of an embodiment of a housing, including a mouthpiece, for an inverted valve device, in accordance with the present invention.
Figure 3:
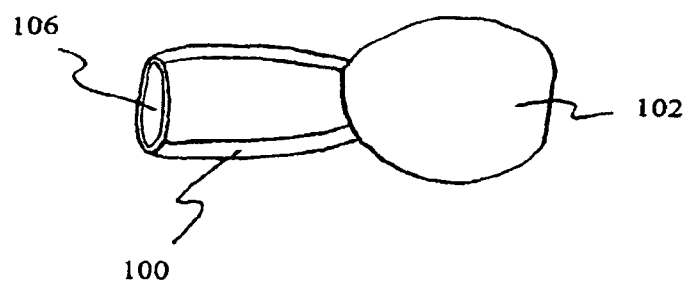
FIG. 3 is a view of the underside of the housing shown in FIG. 2.
Figure 4:
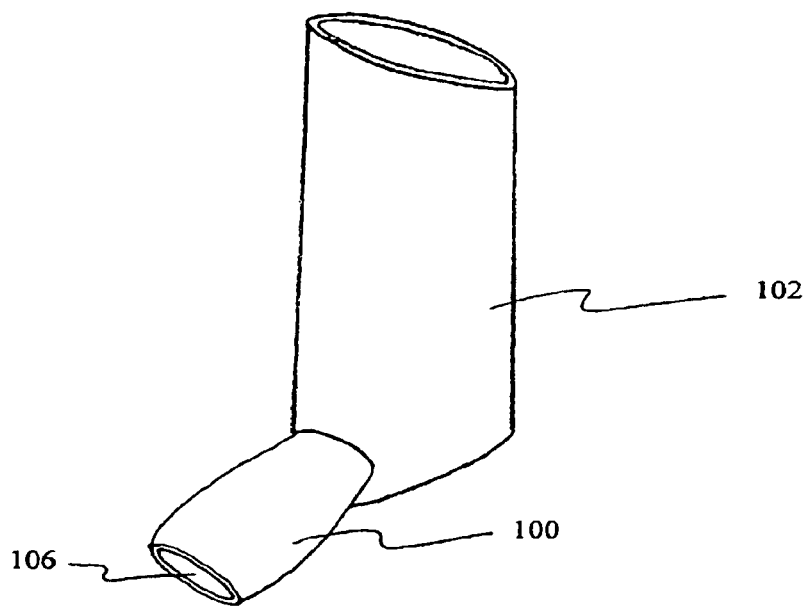
FIG. 4 is a perspective view of the housing shown in FIG. 2.

The device 1, shown in FIG. 1, comprises a substantially cylindrical canister 2 sealed with a cap 3. Both the canister 2 and the cap 3 may be manufactured from a variety of materials. Preferably, the canister and cap are formed from stainless steel or glass. This is because some of the cannabis substances which may be used in the present invention are "aggressive" chemicals and can attack "weaker" container materials. The canister and cap may be lined with a polyester (such as Celanex® 2500) or a lacquer (not shown).

A valve body moulding 4 comprises a cylindrical portion 5, which defines a metering chamber 6 and a stepped flange portion 7, and is formed by injection moulding from Celanex® 2500. The stepped flange portion 7 defines a first and outwardly facing annular seat 8 and a second, inwardly facing annular seat 9. The first annular seat 8 accommodates an annular sealing ring 10 and the second annular seat 9 accommodates a first sealing washer 11. The first sealing washer 11 is located so as to cooperate with the cylindrical portion 5 of the valve body moulding 4, in defining the metering chamber 6.

A base 12 of the cylindrical portion 5 of the valve body moulding 4 completes the boundary to the metering chamber 6 and provides a seat for a second sealing washer 13.

The sealing ring 10 and the first and second sealing washers 11 and 13 can be formed from a butyl rubber, neoprene or one of the elastomers disclosed for such purposes in WO 92/11190.

An elongate, substantially cylindrical and partially hollow valve core 14 is slidably located within the first and second sealing washers 11 and 13 and extends through an orifice 15, defined in the base 12. The valve core 14 is formed by injection moulding from Celanex® 2500.

A stepped inlet passage 16 communicates between a first end 17 of the valve core 14 and an inlet orifice 18, formed through the side of the valve core 14. In a likewise manner, an outlet passage 19 communicates between the second end 20 of the valve core 14 and an outlet orifice 21 formed through the side of the valve core 14. An annular flange 22 extends radially outwardly from the valve core 14 between the inlet and outlet orifices 18 and 21 and adjacent to the outlet orifice 21.

A stainless steel compression coil spring 23 acts between the annular flange 22 and the second sealing washer 13, urging the annular flange 22 into contact with the first sealing washer 11, such that the outlet orifice 21 lies inside the first sealing washer 11 and is thereby isolated from the metering chamber 6. In this position, as shown in FIG. 1, the inlet orifice 18 is located within the metering chamber 6. A flexible tube 24 is engaged within the stepped inlet passage 16 and extends from the valve core 14 to the base of the canister 2 (as shown in FIG. 1). Thus, the inlet orifice 18 is in communication with a region within the canister 2 adjacent to its base 12.

The cap 3 is firmly attached to the canister 2 by crimping and, thus, holds the assembly of the valve body moulding 4, valve core 14, coil spring 23, sealing washers 11 and 13 and sealing ring 10 in place as shown in FIG. 1, with the sealing ring 10 and first sealing washer 11 sufficiently compressed to seal the interior of the device 1 and prevent the egress of its contents.

Downward movement of the valve core, in the direction of arrow A, against the action of the spring 22 will bring the outlet orifice 21 into the metering chamber immediately after the first orifice 18 has been sealed from the metering chamber 6 by the second sealing washer 13.

When filled with a composition in accordance with the present invention, as shown at 25, the device 1 will provide metered doses of the composition when used as follows. The device 1 should be held in the position shown in FIG. 1, so that the composition 25, by virtue of its pressure, enters the metering chamber 6 via the tube 24, the inlet passage 16 and the inlet orifice 18. Subsequent depression of the valve core 14, in the direction of arrow A, seals the inlet orifice 18 and hence the remainder of the canister 2, from the metering chamber 6 and opens the outlet passage to the metering chamber 6, via the outlet orifice 21. Since the composition 25 in the metering chamber 6 is pressurised with the propellant, it will be expelled from the metering chamber 6 through the outlet orifice 21 and the outlet passage 19. If the valve core 14 is then allowed to return to the position shown in FIG. 1, under the influence of the spring 22, the outlet orifice 21 is again sealed from the metering chamber 6 and the metering chamber 6 will be filled with pressurised composition 25 from the canister 2, via the tube 24, stepped inlet passage 16 and inlet orifice 18.

Whilst the foregoing description relates to a device having an upright valve, it is clear that devices with inverted valves may also be used to dispense the compositions of the present invention. Typical suppliers of inverted valves include Bespak plc, King's Lynn, UK, 3M Neotechnic, Clitheroe, UK and Valois Pharm, Le Vaudreuil, France.

Figure 5:
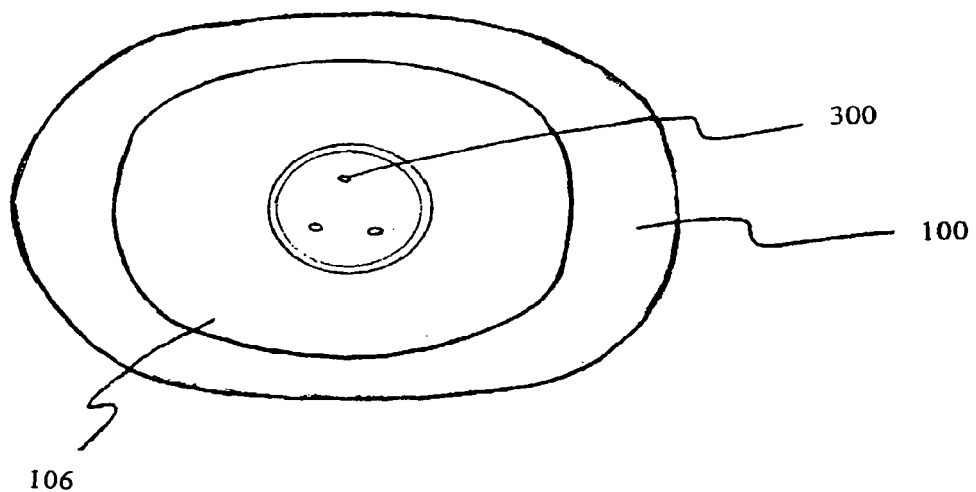
FIG. 5 is a view down the mouthpiece of the housing shown in FIG. 2, the housing containing a spray device with a nozzle having three orifices.
Figure 6:
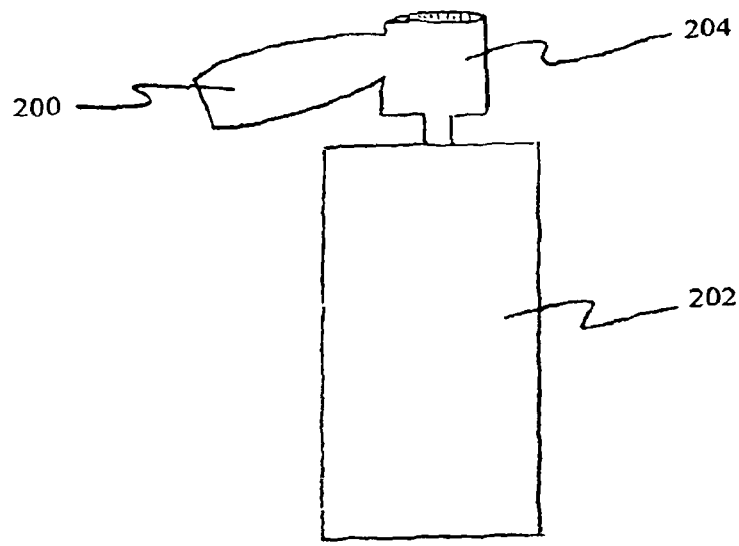
FIG. 6 is a side view of a device with an upright valve, and a mouthpiece according to the present invention.
Figure 7:
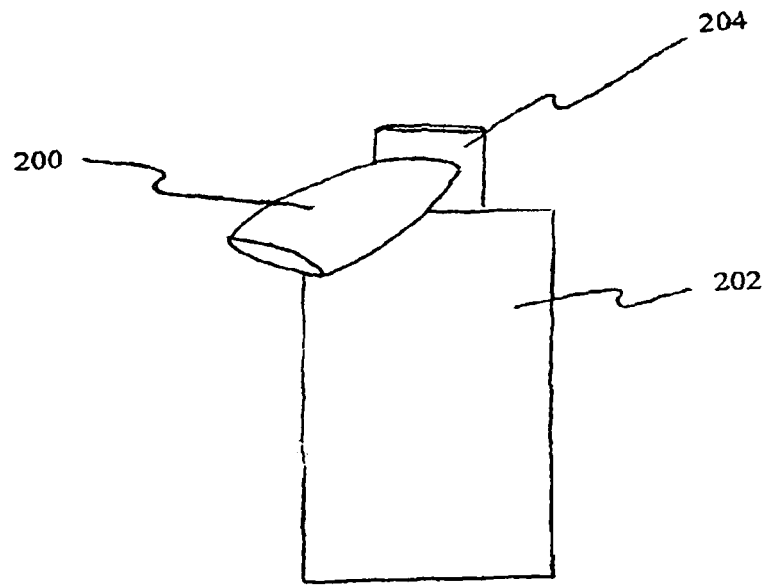
FIG. 7 is a perspective view of the device shown in FIG. 6, wherein the spray device is being activated by downward pressure on the top of the device.

FIGS. 2 to 7 show a mouthpiece according to a preferred embodiment of the present invention. In FIGS. 2 to 5, the mouthpiece 100 is illustrated as being part of the housing 102 which is used to house an inverted valve spray device. In FIGS. 6 and 7, the mouthpiece 200 is used with a conventional upright valve device 202 and is affixed to the moveable button part 204 of the dispensing device.

Thus, when the device is in use, the moveable button 204 is depressed and the mouthpiece will also move relative to the main body of the dispensing device.

Upon activating either type of spray device illustrated in the figures, the composition held within the container is dispensed from the spray device. As it leaves the spray device, the dispensed composition enters the mouthpiece. The mouthpiece then channels the composition to the opening of the mouthpiece 106.

In use, the mouthpiece is preferably placed under the tongue, with the opening of the mouthpiece adjacent to the sublingual area. This ensures that the dispensed composition contacts, almost exclusively, the sublingual area when it leaves the mouthpiece.

The figures illustrate the preferred shape of the mouthpiece. The mouthpiece has a smooth shape, with a gradually increasing cross-sectional area which then decreases again towards the opening.

In FIG. 5, the orifices 300 of the dispensing device are shown. There are three orifices, and each is directional, so that the jets of composition dispensed therefrom converge at a predetermined distance from the outlets themselves.

There now follow some examples of compositions according to the present invention.

Example 1

A composition comprising delta-9-tetrahydrocannabinol (delta-9-THC) with HFC134a suitable for use in a device as described above can be formulated from the following ingredients:

| Component | percent w/w | g/can |
|---|---|---|
| Delta-9-THC | 0.7 | 0.099 |
| Ethanol 96% BP | 13.2 | 1.866 |
| Peppermint oil | 1.4 | 0.205 |
| HFC-134a | 84.7 | 12.02 |
| Total | 100 | 14.19 |

The peppermint oil is added to the delta-9-THC/ethanol solution and mixed thoroughly. 2.17 g of the resulting solution is then placed in the canister 2 and the valve assembly, comprising the valve body moulding 4, first sealing washer 11, second sealing washer 13, spring 22, tube 23, and annular seal 10 are then sealed onto the canister 2 as shown in FIG. 1 by the cap 3. The propellant is then added to the canister by being forced through the valve core 14 at great pressure, and the complete device is then checked for leaks.

Example 2

A second composition comprising delta-9-THC with HFC-134a suitable for use in a device as described above can be formulated from the following ingredients:

| Component | percent w/w | g/can |
|---|---|---|
| Delta-9-THC | 0.164 | 0.010 |
| Ethanol 96% BP | 4.992 | 0.305 |
| HFC-134a | 94.844 | 5.795 |
| Total | 100 | 6.11 |

The delta-9-THC is dissolved in the ethanol in the proportions set out above and 0.315 g of the resulting solution is then placed in a canister 2 and a valve assembly, comprising a valve body moulding 4, first sealing washer 11, second sealing washer 13, spring 22, tube 23, and annular seal 10, is then sealed onto the canister 2 by crimping as shown in FIG. 1 by the cap 3. The propellant (HFC-134a) is then added to the canister, by being forced through the valve core 14 at great pressure, and the complete device is then checked for leaks. After the propellant entered the canister it dissolves the remaining portions of the composition.

Example 3

A third composition comprising delta-9-THC and suitable for use in a device as described above can be formulated from the following ingredients:

| Component | percent w/w | g/can |
|---|---|---|
| Delta-9-THC | 0.164 | 0.010 |
| Ethanol 96% BP | 7.5 | 0.458 |
| HFC-134a | 92.336 | 5.641 |
| Total | 100 | 6.11 |

The delta-9-THC is dissolved in the ethanol in the proportions set out above and 0.315 g of the resulting solution is then placed in a canister 2. A valve assembly (as described in Example 2) is then sealed onto the canister 2 by crimping and the HFC-134a propellant is then added to the canister, by being forced through the valve core 14 at great pressure, and the complete device is then checked for leaks. After the propellant entered the canister it dissolves the remaining portions of the composition.

Example 4

Further compositions comprising delta-9-THC with HFC-134a, suitable for use in a device as described herein, can be formulated in accordance with the details set out in the following table, in which all figures are given on a percent by weight basis.

| | Formulation | | | | |
|---|---|---|---|---|---|
| | A | B | C | D | E |
| delta-9-THC | 0.164 | 0.164 | 0.164 | 0.164 | 0.164 |
| Transcutol | 9.984 | 4.992 | | | |
| Oleyl alcohol | | | 2.496 | | |
| Propylene glycol | | | | 4.992 | |
| Ethanol | | 4.992 | 7.488 | 4.992 | 20.51 |
| p134a | 89.852 | 89.852 | 89.852 | 89.852 | 79.326 |
| Total | 100 | 100 | 100 | 100 | 100 |

Formulations A-E are prepared using a similar technique to that set out in Example 2 above. Briefly, the delta-9-THC is dissolved with the other excipient or excipients (excepting the HFC-134a) and the resulting solution is then placed in a canister 2. A valve assembly is then sealed onto the canister 2 by crimping and the HFC-134a propellant is then added to the canister 2, by being forced through the valve core 14 at great pressure. After the propellant enters the canister 2, it dissolves the remaining portions of each composition.

Although only delta-9-tetrahydrocannabinol is referred to in the above mentioned examples, other cannabis active agents previously discussed in this application may be substituted therefor in quantities which would dissolve at least partially in the propellant/co-solvent mixture.

What is claimed is:

1. A metered valve pump spray device consisting essentially of a liquid cannabis extract, in carriers consisting essentially of propylene glycol, and ethanol, wherein said metered valve pump spray device is adapted to spray a dose towards a patient's sublingual mucosa from the orifice of the device, and is adapted to dispense particles of a particular size, thereby optimizing the sublingual uptake in the patient.

* * * * *